United States Patent
Denni-Dischert et al.

(10) Patent No.: US 7,317,100 B2
(45) Date of Patent: Jan. 8, 2008

(54) EPOTHILONE DERIVATIVES

(75) Inventors: Donatienne Denni-Dischert, Wettolsheim (FR); Andreas Floersheimer, Dornach (CH); Ernst Kuesters, Eschbach (DE); Lukas Oberer, Tenniken (CH); Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 170 days.

(21) Appl. No.: 10/538,200

(22) PCT Filed: Dec. 22, 2003

(86) PCT No.: PCT/EP03/14747

§ 371 (c)(1),
(2), (4) Date: Jun. 9, 2005

(87) PCT Pub. No.: WO2004/056832

PCT Pub. Date: Jul. 8, 2004

(65) Prior Publication Data
US 2006/0014796 A1 Jan. 19, 2006

(30) Foreign Application Priority Data
Dec. 23, 2002 (GB) .................... 0230024.2

(51) Int. Cl.
*C07D 491/00* (2006.01)
*C07D 313/00* (2006.01)
*C07D 493/00* (2006.01)
*C07D 69/76* (2006.01)
*C07D 69/95* (2006.01)

(52) U.S. Cl. .................. 540/462; 549/270; 549/554; 549/513; 560/51; 568/449

(58) Field of Classification Search ............ 549/270, 549/554, 513; 540/462, 480, 481; 514/183, 514/450; 560/51; 568/449
See application file for complete search history.

(56) References Cited

FOREIGN PATENT DOCUMENTS

| JP | 03 048641 | 3/1991 |
| WO | 98/25929 | 6/1998 |
| WO | 99/07692 | 2/1999 |
| WO | 99/65913 | * 12/1999 |
| WO | 03/022844 | 3/2003 |

OTHER PUBLICATIONS

Hardt et al., Journal of Natural Products, "New natural Epothilones form Sorangium cellullosum, strains So ce90/B2 and So ce90/D13: Isolation, structure elucidation, and SAR studies", vol. 64, pp. 847-856, 2001.*
Dermer et al., Bio/Technology, 1994, vol. 12, p. 320.*
Freshney et al., Culture of animal cells, A manual of basic technique, Alan R. Liss, Inc., 1983, New York, pp. 1-6.*
Hardt et al., "New natural epothilones from sorangium cellyulosum, Straqins so ce90/B2 and So ce90/D13: Isolation, structure elucidation, and SAR studies," Journal of Natural Products, XX, XX, vol. 64(7), pp. 847-856 (2001).
Nicolaou et al., "Chemical biology of epothilones," Angewandte Chemie. International Edition, Verlag Chemie, vol. 37(15), pp. 2014-2045 (1998).
Su et al., "Structure-activity relationships of the epothilones and the first in vivo comparison with praclitaxel," Angewandte Chemie. International Edition, Verlag Chemie. Weinheim DE, vol. 36(19), pp. 2093-2096 (1997).
Ali et al., "Formal Syntheses of Cryptophycin A and Arenastatin A," Tetrahedron Letters, vol. 38(10), pp. 1703-1706 (1997.
Oppotzer et al., "Efficient Asymmetric Synthesis of Anti-Aldols from Bornanesultam Derived Boryl Enolates," Tetrahedron Leters, vol. 34(27), pp. 4321-4324 (1993).
Koch et al., "Diastereoselective Titanium Enolate Aldol Reaction for the Total Synthesis of Epothilones," Organic Letters, vol. 4(22), pp. 3811-3814 (2002).
Regueiro-Ren et al., "SAR and pH Stability fo Cyano-Substituted Epothilones," Organic Letters, vol. 4(22), pp. 3815-3818 (2002).
de Jesus Oliveira et al., "Diastereoselective formation of a quaternary center ij a pyroglutamate derivative. Formal synthesis of Monatin," Tetrahedron Letters, vol. 42, pp. 6793-6796 (2001).
Chappell et al., "Probing the SAR of dEpoB via Chemical Synthesis: A Total Synthesis Evaluation of C26-(1,3-dioxolanyl)-12,13-desoxyepothilone B," J. Org. Chem., vol. 67, pp. 7730-7736 (2002).
Patent Abstracts of Japan, vol. 015, No. 193 (C-0832), May 17, 1991.

* cited by examiner

Primary Examiner—Janet Andres
Assistant Examiner—Niloofar Rahmani

(57) ABSTRACT

The present invention relates to C4-demethyl-epothilones or C4-bisnor-epothilones of Formula (I), their pharmaceutical use, pharmaceutical composition containing the same and methods for their preparation.

4 Claims, No Drawings

EPOTHILONE DERIVATIVES

The present invention relates to C4-demethyl-epothilones or C4-bisnor-epothilones and their pharmaceutical use, pharmaceutical composition containing the same and methods for their preparation.

Despite the widespread use of Taxol® and Taxotere® in the treatment of many different tumor types, the impact of taxanes on patient survival has been modest, and the overwhelming majority of metastatic solid tumors remain incurable. Taxane treatment is associated with a number of significant side-effects, and the effectiveness of taxanes can be severely limited by the rapid development of drug resistance mechanisms. In view of these limitations as well as the side-effects commonly observed with standard combination therapies, there is a clear need for the identification of novel cytotoxic anti-cancer agents exhibiting an improved overall profile including spectrum of anti-tumor activity, efficacy against multi-drug resistant tumors, safety and tolerability.

The microtubule-stabilizing effect of the epothilones was first described by Bollag et al., Cancer Research 55, 1995, 2325-33. A suitable treatment schedule for the treatment of different types of tumors, especially tumors which are refractory to the treatment by other chemotherapeutics, in particular TAXOL™, using an epothilone, in particular epothilone A or B, is described in WO 99/43320. D. Su, A. Balog et al. discussed in Angew. Chem. Int. Ed. Engl. 1997, 36, pages 2093 to 2096, the structure-activity relationship of the class of the epothilones. On pages 2094 of said publication, they inter alia concluded that a modification of the structure of the natural compounds at the carbon atoms indicated as C1 to C8 results in a major loss of cytotoxicity and of loss of activity in the tubulin/microtubule system. Surprisingly, it has now been found that the C4-(demethyl or bisnor)-epothilones of formula I have beneficial pharmacological properties and can be used for the treatment of proliferative diseases.

Hence, the present invention relates to C4-(demethyl or bisnor)-epothilones of formula I

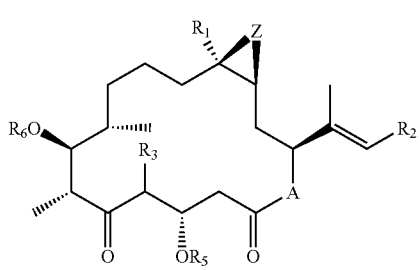
(I)

wherein A represents O or $NR_7$,
$R_1$ is hydrogen or lower alkyl which is unsubstituted or substituted by hydroxy, lower acyloxy, lower alkanoyl in free or protected form, lower alkoxy, halogen, amino, lower alkyl amino, di-lower alkyl amino, or lower acyl amino,
$R_2$ is unsubstituted or substituted heteroaryl having at least one nitrogen atom,
$R_3$ represents hydrogen or lower alkyl, preferably methyl,
$R_5$ and $R_6$ are hydrogen, and
$R_7$ is hydrogen or lower alkyl,
Z is O or a bond, under the proviso that
when $R_2$ is 2-methyl-thiazolyl and Z is O, $R_1$ represents lower alkyl which is unsubstituted or substituted by hydroxy, lower acyloxy, lower alkoxy, halogen, amino, lower alkyl amino, di-lower alkyl amino or lower acyl amino, and
when $R_2$ is 2-methyl-thiazolyl and Z is a bond, $R_1$ represents lower alkyl which is substituted by hydroxy, lower acyloxy, lower alkoxy, halogen, amino, lower alkyl amino, di-lower alkyl amino or lower acyl amino,
and to the salts thereof.

The general terms used herein before and hereinafter preferably have within the context of this disclosure the following meanings, unless otherwise Indicated:

Where the plural form is used for compounds, salts, and the like, this is taken to mean also a single compound, salt, or the like.

Any asymmetric carbon atoms may be present in the (R)—, (S)— or (R,S)-configuration, preferably in the (R)— or (S)-configuration. The compounds may thus be present as mixtures of isomers or as pure isomers, preferably as enantiomer-pure diastereomers.

The formula I represents two stereoisomers. The present invention relates to both such stereoisomers represented by formula Ia and Ib,

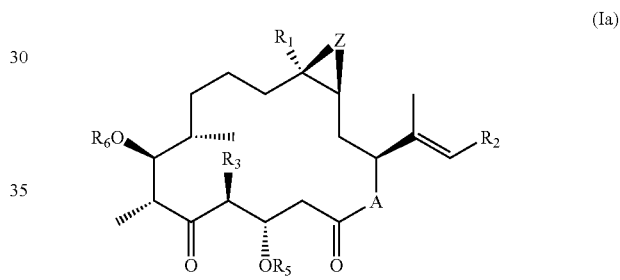
(Ia)

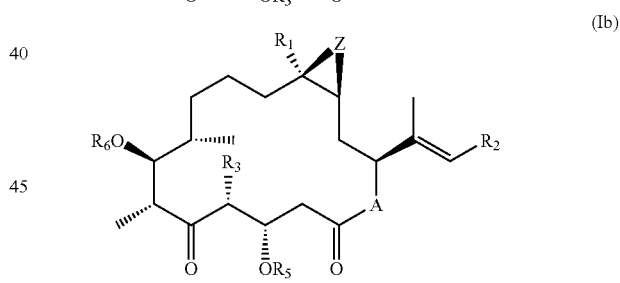
(Ib)

wherein the symbols and radicals have the meanings as provided for a compound of formula I above, preferably to a compound of formula Ia.

The prefix "lower" denotes a radical having up to and including a maximum of 7, especially up to and including a maximum of 4 carbon atoms, the radicals in question being either linear or branched with single or multiple branching.

"Halogen" is fluorine, chlorine, bromine or iodine.

"Alkyl" is preferably lower alkyl.

"Lower alkyl" is linear or branched; e.g. It is butyl, such as n-butyl, sec-butyl, isobutyl, tert-butyl, propyl, such as n-propyl or isopropyl, ethyl or methyl. Preferably lower alkyl is methyl, ethyl, n-propyl, isopropyl or tert-butyl.

"Alkoxy" is preferably lower alkoxy, e.g. methoxy, ethoxy, isopropoxy or tert-butoxy.

"Acyl" is preferably lower acyl, e.g. acetyl.

"Lower alkanol" is preferably methanol, ethanol, 1-propanol, 2-propanol, 1-butanol or 2-butanol.

"Lower alkane" is in particular pentane, hexane or heptane.

"Heteroaryl having at least one nitrogen atom" represents a mono- or bicyclic group comprising at least one, two or three ring nitrogen atoms and zero or one oxygen atom and zero or one sulfur atom, which group is unsaturated in the ring binding the heteroaryl radical to the rest of the molecule in formula I and is preferably a group, where the binding ring preferably has 5 to 12, more preferably 5 or 6 ring atoms; and which may be unsubstituted or substituted by one or more, especially one or two, substituents, preferably selected from halogen, alkoxy, alkylthio, hydroxy, alkanoyl or, most preferably, alkyl. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, 3H-indolyl, indolyl, isoindolyl, oxazolyl, isoxazolyl, thiazolyl, isothiazolyl, benzo[b]thiazolyl, triazolyl, tetrazolyl, benzo[b]oxazolyl and benzo[d]pyrazolyl.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

The compounds of formula I have valuable pharmacological properties, as described hereinbefore and hereinafter.

The efficacy of the compounds of formula I as inhibitors of microtubule depolymerisation may be proved as follows:

Stock solutions of the test compounds (10 mM) are prepared in DMSO and stored at −20° C. Microtubule protein (i.e. tubulin plus microtubule-associated proteins) is extracted from pigs' brain by two cycles of temperature-dependent depolymerisation/polymerisation, as known (see Weingarten et al., Biochemistry 1974; 13: 5529-37). Working stock solutions of porcine microtubule protein are then stored at −70° C. The degree of test-compound-induced polymerisation of porcine microtubule protein is determined basically as already known (see Lin et al., Cancer Chem. Pharm. 1996; 38:136-140). To summarise, a working aliquot of porcine microtubule protein is rapidly thawed and then diluted to 2× final desired concentration in ice-cold 2× MEM buffer (200 ml MES, 2 mM EGTA, 2 mM $MgCl_2$, pH 6.7) [MES=2-morpholinoethanesulphonic acid, EGTA=ethylene glycol-bis-2(2-aminoethyl)-tetraacetic acid]. Drug or vehicle (DMSO, final concentration 5%) is diluted in water at room temperature to 2× the final desired concentration in a 0.5 ml eppendorf tube, and then put on ice. Following addition of an equal volume (50 µl) of microtubule protein (2× final desired concentration in 2× MEM buffer), the polymerization reaction is started by transferring the incubation mixtures to a room-temperature water bath for 5 min. The reaction mixtures are then placed in an Eppendorf microcentrifuge (model 5415 C) and incubated for an additional 15 min at room temperature. The samples are then centrifuged for 15 min at 14,000 rpm at room temperature. As an indirect measure for microtubule protein polymerization, the protein concentration of the supernatant (containing the remainder of non-polymerized, soluble microtubule protein) is determined by the Lowry method (DC Assay Kit, Bio-Rad Laboratories, Hercules, Calif.) and the optical density of the colour reaction is measured at 750 nm with a SpectraMax 340 photometer (Molecular Devices, Sunnydale, Calif.). The reduction in optical density by test drug is compared to that induced by 25 µM epothilone B (positive control, 100% polymerization). Vehicle-treated samples serve as negative control (0% polymerization). Polymerization activity of test drug is expressed in percentage relative to the positive control (100% polymerization).

The efficacy against tumour cells may be demonstrated in the following way:

Stock solutions of the test compounds (10 mM) are prepared in DMSO and stored at −20° C. Human KB-31 and (multidrug-resistant, P-gp170 overexpressing) KB-8511 epidermoid carcinoma cells originate from Dr. M. Baker, Roswell Park Memorial institute (Buffalo, N.Y., USA) (description: see also Akiyama et al., Somat. Cell. Mol. Genetics 11, 117-126 (1985) and Fojo A., et al., Cancer Res. 45, 3002-3007 (1985) -KB-31 and KB-8511 are both derivatives of the KB cell line (ATCC). KB 31 cells may be cultivated in monolayers using RPMI-1640 medium (Amimed, BioConcept, Allschwil, Switzerland) with 10% foetal calf serum (Amimed, BioConcept, Allschwil, Switzerland), L-glutamine (Amimed, BioConcept, Allschwil, Switzerland), penicillin (50 units/ml) and streptomycin (50 µg/ml (Amimed, BioConcept, Allschwil, Switzerland). KB-8511 is a variant derived from the KB-31 cell line, which was obtained using colchichine treatment cycles, and has an approximately 40 times relative resistance to colchichine compared with KB-31 cells (Akiyama et al., Somat. Cell. Mol. Genetics 11, 117-126 (1985) and Fojo A., et al., Cancer Res. 45, 3002-3007 (1985)). The cells are incubated at 37° C. in an incubator with 5% v/v $CO_2$ and at 80% relative humidity with RPMI-1640 medium complemented as described above. The cells are seeded in a quantity of $1.5 \times 10^3$ cells/well in 96-well microtitre plates, and incubated over night. Serial dilutions of the test compounds in culture medium are added on day 1. The plates are then incubated for a further 4 days, after which the cells are fixed with 3.3% v/v glutaraldehyde, washed with water and dyed with 0.05% w/v methylene blue. After washing, the dye is eluted with 3% HCl and the optical density measured at 665 nm with a SpectraMax 340 (Molecular Devices, Sunnyvale, Calif.). IC50 values are determined by adaptation of mathematical curves, using the SoftProprogramme (Version 2.0 or later; Molecular Devices, Sunnyvale, Calif.) and using the formula [(OD treated)−(OD start)]/[(OD control)−(OD start)]× 100. The IC50 is defined as the concentration of a test compound at the end of the incubation period, which led to 50% inhibition of the net increase in cell mass compared to control cultures. Compounds of formula I thus preferably show an IC50 in the range of 0.15 and 15 nM, preferably between 0.25 and 5 nM.

The in vivo efficacy may be demonstrated as follows: The models used are xeno-transplants of tumours, such as KB-31 or KB-8511 epidermoid tumours, in mice. The anti-tumour efficacy of the test compounds may be measured in female BLB/c nu/nu mice for example against the corresponding subcutaneously transplanted cell line. To this end, tumour fragments of about 25 mg are implanted into the left side of each of the mice (for example 6 animals per dose). The test compound is administered for example on day 11 after transplantation in different dosages (for example 0.1; 0.5; 1; 5 and 10 mg/kg), if desired repeating the administration, if required several times, after between two days and two weeks. The volumes of the tumours are determined for example after about 2 to 4 weeks (e.g. two weeks after the start of treatment). The tumour volumes are calculated by measuring the tumour diameter along two vertically arranged axes and according to published methods (see Evans et al., Brit. J. Cancer 45, 466-8 (1982)). The anti-tumour efficacy is determined as the mean increase in tumour volume of the treated animals divided by the mean increase in tumour volume of the untreated animals (controls) and, after multiplication by 100, is expressed as T/C %. Tumour regression (given in %) is calculated as the smallest mean tumour volume (Vt) in relation to the mean tumour volume at the start of treatment (Vo) according to the formula % regression=$[1-(Vt/Vo)] \times 100$.

In this case also, other cell lines can be used, for example those named above in the demonstration of efficacy against tumour cells.

On the basis of their efficacy as inhibitors of tubulin depolymerization the C4-desmethyl epothilone of the formula I are effective against a number of proliferative diseases, such as solid tumor diseases, liquid tumor disases (like leukemia) or psoriasis.

The term "solid tumor disease" especially means breast cancer, cancer of the colon and generally the GI tract including gastric cancer, hepatoma; lung cancer, in particular small-cell lung cancer and non-small-cell lung cancer, renal cancer, mesothelioma, glioma, squamous cell carcinoma of the skin, head and neck cancer, genitourinary cancer, e.g. cervical, uterine, ovarian, testicles, prostate or bladder cancer; Hodgkin's disease, carcinoid syndrome or Kaposi's sarcoma. In a preferred embodiment of the invention, the solid tumor disease to be treated is selected from breast cancer, colorectal cancer, ovarian cancer, renal cancer, lung cancer, especially non-small-cell lung cancer, and glioma. The C4-desmethyl epothilone of the formula I disclosed herein are also suitable to prevent the metastatic spread of tumors and the growth or development of micrometastases, in particular due to their ant-angiogenic activity.

A C4-desmethyl epothilone of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A C4-desmethyl epothilone of formula I can be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain a patient's status after tumor regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, erg. PKI166, the VEGF receptor tyrosine kinase, e.g. PTK787, or the PDGF receptor tyrosine kinase, e.g. STI571, a cytokine, a negative growth regulator, such as TGF-β or IFN-β, an aromatase inhibitor, e.g. letrozole or anastrozole, an inhibitor of the interaction of an SH2 domain with a phosphorylated protein, antiestrogens, topolsomerase I inhibitors, such as irinotecan, topoisomerase II inhibitors, other microtubule active agents, e.g. paclitaxel, or (+)-discodermolide, alkylating agents, antineoplastic antimetabolites, such as gemcitabine or capecitabine, platin compounds, such as carboplatin or cisplatin, anti-anglogenic compounds, gonadorelin agonists, anti-androgens, bisphosphonates, e.g. AREDIA® or ZOMETA®, and trastuzumab. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

In general, the invention relates also to the use of a C4-desmethyl epothilone of formula I or a salt thereof for the stabilization of the microtubule cell skeleton, either In vitro or In vivo.

With the groups of preferred C4-desmethyl epothilone of formula I and salts thereof mentioned hereinafter, definitions of substituents from the general definitions mentioned herein before may reasonably be used, for example, to replace more general definitions with more specific definitions or especially with definitions characterized as being preferred.

In particular, the invention relates to a C4-desmethyl-epothilone of formula Ia or Ib

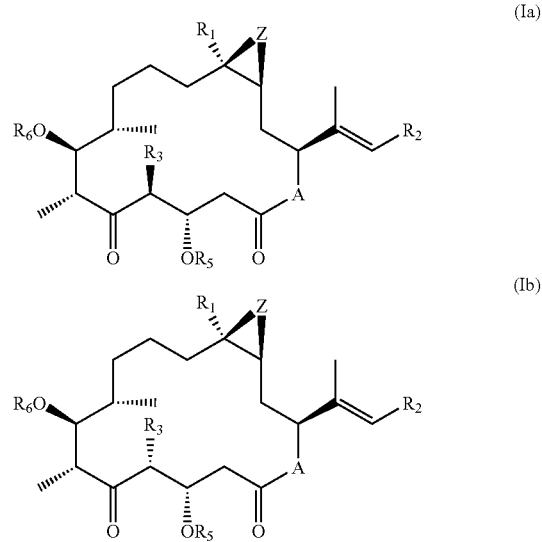

wherein A represents O or NR$_7$,
R$_1$ is hydrogen or lower alkyl which is unsubstituted or substituted by hydroxy, lower acyloxy, lower alkanoyl in free or protected form, lower alkoxy, halogen, amino, lower alkyl amino, di-lower alkyl amino, or lower acyl amino,
R$_2$ is unsubstituted or substituted heteroaryl having at least one nitrogen atom,
R$_3$ represents hydrogen or lower alkyl, preferably lower alkyl
R$_5$ and R$_6$ are hydrogen, and
R$_7$ is hydrogen or lower alkyl,
Z is O or a bond,
under the proviso that when R$_2$ is 2-methyl-thiazolyl and Z is O, R$_1$ represents lower alkyl which is unsubstituted or substituted by hydroxy, lower acyloxy, lower alkoxy, halogen, amino, lower alkyl amino, di-lower alkyl amino or lower acyl amino, and when R$_2$ is 2-methyl-thiazolyl and Z is a bond, R$_1$ represents lower alkyl which is substituted by hydroxy, lower acyloxy, lower alkoxy, halogen, amino, lower alkyl amino, di-lower alkyl amino or lower acyl amino,
and to the salts thereof.

Especially, the invention relates to C4-(demethyl or bisnor)-epothilones of formula I or of formula Ia or Ib, wherein
A represents O or NR$_7$,
R$_1$ is hydrogen or lower alkyl which is unsubstituted or substituted by hydroxy, lower acyloxy, lower alkanoyl in free or protected form, lower alkoxy, halogen, amino, lower alkyl amino, di-lower alkyl amino, or lower acyl amino,
R$_2$ is thiazolyl, oxazolyl, pyridyl, benzothiazolyl, benzoxazolyl or benzoimidazolyl, which in each case is substituted or unsubstituted,
R$_3$ represents hydrogen or tower alkyl, preferably lower alkyl
R$_5$ and R$_6$ are hydrogen, and
R$_7$ is hydrogen or lower alkyl,
Z is O or a bond,
under the proviso that
when R$_2$ is 2-methyl-thiazolyl and Z is O, R$_1$ represents lower alkyl which is unsubstituted or substituted by hydroxy, lower acyloxy, lower alkoxy, halogen, amino, lower alkyl amino, di-lower alkyl amino or lower acyl amino, and
when R$_2$ is 2-methyl-thiazolyl and Z is a bond, R$_1$ represents lower alkyl which is substituted by hydroxy, lower acyloxy, lower alkoxy, halogen, amino, lower alkyl amino, di-lower alkyl amino or lower acyl amino,
and the salts thereof.

Preferred are C4-(demethyl or bisnor)-epothilones of formula I or of formula Ia or Ib, wherein
A represents O or NR$_7$,
R$_1$ is hydrogen or lower alkyl which is unsubstituted or substituted by hydroxy, lower acyloxy, lower alkoxy, halogen, amino, lower alkyl amino, di-lower alkyl amino or lower acyl amino,
R$_2$ is thiazolyl, oxazolyl, pyridyl, benzothiazolyl, which in each case is substituted or unsubstituted,
R$_3$ represents hydrogen or lower alkyl, preferably lower alkyl
R$_5$ and R$_6$ are hydrogen, and
R$_7$ is hydrogen or lower alkyl,
Z is O or a bond,
under the proviso that
when R$_2$ is 2-methyl-thiazolyl and Z is O, R$_1$ represents lower alkyl which is unsubstituted or substituted by hydroxy, lower acyloxy, lower alkoxy, halogen, amino, lower alkyl amino, di-lower alkyl amino or lower acyl amino, and
when R$_2$ is 2-methyl-thiazolyl and Z is a bond, R$_1$ represents lower alkyl which is substituted by hydroxy, lower acyloxy, lower alkoxy, halogen, amino, lower alkyl amino, di-lower alkyl amino or lower acyl amino,
and the salts thereof.

More preferred are C4-(demethyl or bisnor)-epothilones of formula I or of formula Ia or Ib, wherein
A represents O,
R$_1$ is hydrogen or lower alkyl,
R$_2$ is 2-methyl-thiazolyl, 2-ethyl-thiazolyl, 2-methylthio-thiazolyl, 2-aminomethyl-thiazolyl, 2-dimethylamino-thiazolyl, 2-fluoromethyl-thiazolyl, 2-methyl-oxazolyl, 3-methyl-pyridinyl, 2-methyl-benzothiazolyl,
R$_3$ represents hydrogen lower alkyl, preferably lower alkyl,
R$_5$ and R$_6$ are hydrogen, and
Z is O or a bond,
under the proviso that when R$_2$ is 2-methyl-thiazolyl, Z is O and R$_1$ represents lower alkyl, and the salts thereof.

Even more preferred are C4-(demethyl or bisnor)-epothilones of formula I or of formula Ia or Ib, wherein
A represents O,
R$_1$ is hydrogen or lower alkyl,
R$_2$ is 2-methyl-thiazolyl, 2-ethyl-thiazolyl, 2-methylthio-thiazolyl, 2-aminomethyl-thiazolyl, 2-dimethylamino-thiazolyl, 2-fluoromethyl-thiazolyl, 2-methyl-oxazolyl, 3-methyl-pyridinyl, 2-methyl-benzothiazolyl,
R$_3$ represents methyl,
R$_5$ and R$_6$ are hydrogen, and
Z is O or a bond,
under the proviso that when R$_2$ is 2-methyl-thiazolyl, Z is O and R$_1$ represents lower alkyl,
and the salts thereof.

Furthermore, the present invention relates to the use of a C4-desmethyl-epothilone of formula I or of formula Ia or Ib or a pharmaceutically acceptable salt thereof for the treatment of a tumour disease and for the preparation of a pharmaceutical product for the treatment of a tumour disease.

Additionally, the present invention provides a method for the treatment of warm-blooded animals, including humans, in which an therapeutically effective amount of a C4-desmethyl-epothilone of the formula I or of formula Ia or Ib or a pharmaceutically acceptable salt of such a compound is administered to a warm-blooded animal suffering from a tumour disease.

Epothilones of formula I, wherein A represents O or NR$_7$, R$_1$ is hydrogen or lower alkyl which is unsubstituted or substituted by hydroxy, lower acyloxy, lower alkoxy, halogen, amino, lower alkyl amino, di-lower alkyl amino, lower acyl amino, R$_2$ is unsubstituted or substituted heteroaryl, R$_7$ is hydrogen or lower alkyl, R$_5$ and R$_6$ are hydrogen and Z is O or a bond can be prepared, e.g., by a process wherein an aldehyde of formula II,

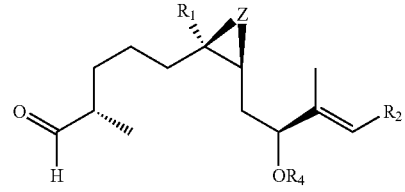

(II)

wherein $R_1$, $R_2$ and Z have the meanings as provided above for a compound of formula I and $R_4$ is a protecting group, is reacted in a first step with an ethylketone of formula III,

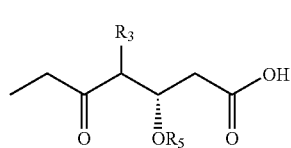
(III)

wherein $R_5$ is H or a protecting group different or identical to $R_4$ and $R_3$ has the meaning as provided above for a compound of formula I, to provide the aldol of formula IV,

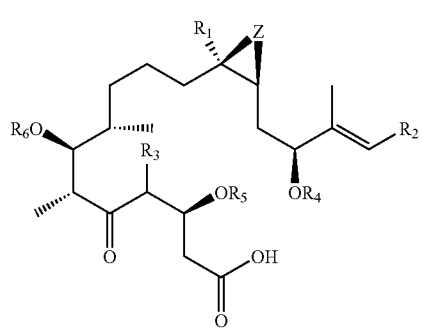
(IV)

wherein $R_1$, $R_2$, $R_3$ and Z have the meanings as provided above for a compound of formula I, $R_4$ a protecting group, $R_5$ is H or a protecting group different or identical to $R_4$ and $R_6$ is hydrogen, which aldol of formula IV is reacted in a second step with a reagent capable to introduce a protecting group which is different or identical to $R_4$ furnishing a carboxylic acid of formula IV, wherein $R_1$, $R_2$, $R_3$ and Z have the meanings as provided above for a compound of formula I, $R_4$ a protecting group and $R_5$ is H or $R_5$ and $R_6$ are protecting groups different or identical to $R_4$, which carboxylic acid of formula IV is reacted in a third step with a reagent capable to remove the protecting group $R_4$ under conditions which do not result in the removal of the protecting groups $R_5$ and $R_6$ providing a carboxylic acid of formula IV, wherein $R_1$, $R_2$, $R_3$ and Z have the meanings as provided above for a compound of formula I, $R_4$ is hydrogen and $R_5$ is H or $R_5$ and $R_6$ are protecting groups, which carboxylic acid of formula IV in a fourth step is subject of a macrolactonisation reaction providing the epothilone of formula I, wherein $R_1$, $R_2$, $R_3$ and Z have the meanings as provided above for a compound of formula I, A is O and $R_5$ is H or $R_5$ and $R_6$ are protecting groups, which epothilone of formula I is reacted in a fifth step with a reagent capable to remove the protecting groups $R_5$ (if existing) and $R_6$ furnishing an epothilone of formula I, wherein $R_1$, $R_2$, $R_3$, $R_5$, $R_6$ and Z have the meanings as provided above for a compound of formula I and A is O, which epothilone of formula I is, optionally, further transformed into an epothilone of formula I wherein $R_1$, $R_2$, $R_3$, $R_5$, $R_6$ and Z have the meanings as provided above for a compound of formula I and A is $NR_7$, wherein $R_7$ is hydrogen or lower alkyl.

Epothilones of formula Ia or Ib, wherein A represents O or $NR_7$, $R_1$ is hydrogen or lower alkyl which is unsubstituted or substituted by hydroxy, lower acyloxy, lower alkoxy, halogen, amino, lower alkyl amino, di-lower alkyl amino, lower acyl amino, $R_2$ is unsubstituted or substituted heteroaryl, $R_7$ is hydrogen or lower alkyl, $R_5$ and $R_6$ are hydrogen and Z is O or a bond can be prepared, e.g., by a process wherein an aldehyde of formula II,

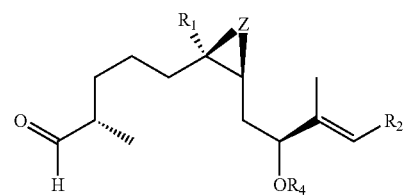
(II)

wherein $R_1$, $R_2$ and Z have the meanings as provided above for a compound of formula I and $R_4$ is a protecting group, is reacted in a first step with an ethylketone of formula IIIa or IIIb, respectively,

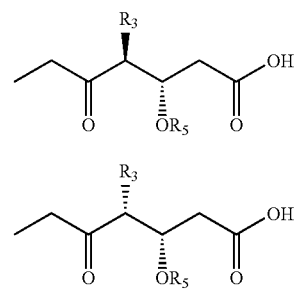
(IIIa)

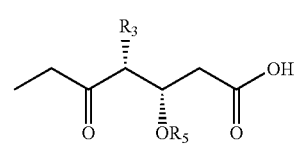
(IIIb)

wherein $R_5$ is H or a protecting group different or identical to $R_4$ and $R_3$ has the meaning as provided above for a compound of formula I, to provide the aldol of formula IVa or IVb, respectively,

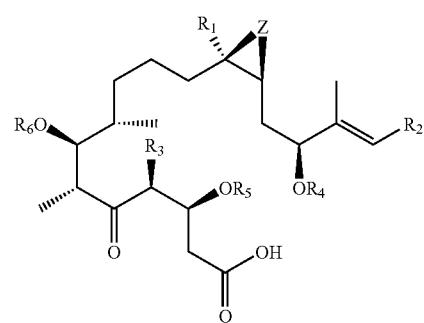
(IVa)

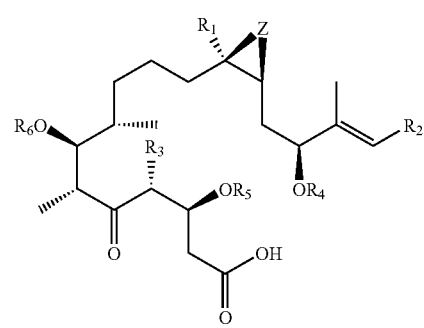
(IVb)

wherein $R_1$, $R_2$, $R_3$ and Z have the meanings as provided above for a compound of formula I, $R_4$ a protecting group, $R_5$ is H or a protecting group different or identical to $R_4$ and $R_6$ is hydrogen, which aldol of formula IVa or IVb is reacted in a second step with a reagent capable to introduce a protecting group which is different or identical to $R_4$ furnishing a carboxylic acid of formula IVa or IVb, wherein $R_1$, $R_2$, $R_3$ and Z have the meanings as provided above for a compound of formula I, $R_4$ a protecting group and $R_5$ is H or $R_5$ and $R_6$ are protecting groups different or identical to $R_4$, which carboxylic acid of formula IVa or IVb is reacted in a third step with a reagent capable to remove the protecting group $R_4$ under conditions which do not result in the removal of the protecting groups $R_5$ and $R_6$ providing a carboxylic acid of formula IVa or IVb, wherein $R_1$, $R_2$, $R_3$ and Z have the meanings as provided above for a compound of formula I, $R_4$ is hydrogen and $R_5$ is H or $R_5$ and $R_6$ are protecting groups, which carboxylic acid of formula IVa or IVb in a fourth step is subject of a macrolactonisation reaction providing the epothilone of formula Ia or Ib, wherein $R_1$, $R_2$, $R_3$ and Z have the meanings as provided above for a compound of formula I, A is O and $R_5$ is H or $R_5$ and $R_6$ are protecting groups, which epothilone of formula Ia or Ib is reacted in a fifth step with a reagent capable to remove the protecting groups $R_5$ and $R_6$ furnishing an epothilone of formula Ia or Ib, wherein $R_1$, $R_2$, $R_3$, $R_5$, $R_6$ and Z have the meanings as provided above for a compound of formula I and A is O, which epothilone of formula Ia or Ib is, optionally, further transformed into an epothilone of formula Ia or Ib wherein $R_1$, $R_2$, $R_3$, $R_5$, $R_6$ and Z have the meanings as provided above for a compound of formula I and A is $NR_7$, wherein $R_7$ is hydrogen or lower alkyl.

Protecting Groups

If one or more other functional groups, for example carboxy, hydroxy, amino, or mercapto, are or need to be protected in a compound mentioned herein, because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, N.Y. 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/1, Georg Thieme Verlag, Stuttgart 1974, in H.-D. Jakubke and H. Jescheit, "Aminosäuren, Peptide, Proteine" (*Amino acids, peptides, proteins*), Veriag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

$R_5$ can be a protecting group which is different or identical to $R_4$. In case both protecting groups are identical, such groups have to represent protection groups which can be splitt off from the compound of formula I sequentielly, i.e. reaction conditions must exist for such groups allowing to replace $R_4$ by hydrogen or another protecting group under which the protecting group $R_5$ remains in the compound of formula I.

The transformation of epothilone B to the corresponding lactam is disclosed in Scheme 21 (page 31, 32) and Example 3 of WO 99/02514 (pages 48-50). The transformation of a compound of formula I which is different from epothilone B into the corresponding lactam can be accomplished analogously. Corresponding epothilone derivatives of formula I wherein $R_4$ is lower alkyl can be prepared by methods known in the art such as a reductive alkylation reaction starting from the epothilone derivative wherein $R_4$ is hydrogen.

Additional Process Steps

In the additional process steps, carried out as desired, functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent.

Salts can usually be converted to free compounds, e.g. by treating with suitable basic agents, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates.

General Process Conditions

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to −60° C., at room temperature, at −20 to 40° C. or at the boiling point of the solvent used, under atmospheric pressure or in a closed vessel, where appropriate under pressure, and/or in an inert atmosphere, for example under argon or nitrogen.

Salts may be present in all starting compounds and transients, if these contain salt-forming groups. Salts may also be present during the reaction of such compounds, provided the reaction is not thereby disturbed.

At all reaction stages, isomeric mixtures that occur can be separated into their individual isomers, e.g. diastereomers or enantiomers, or into any mixtures of isomers, e.g. racemates or diastereomeric mixtures, typically as described under "Additional process steps".

The solvents from which those can be selected which are suitable for the reaction in question include for example water, esters, typically lower alkyl-lower alkanoates, e.g. diethyl acetate, ethers, typically aliphatic ethers, e.g. diethylether, or cyclic ethers, e.g. tetrahydrofuran, liquid aromatic hydrocarbons, typically benzene or toluene, alcohols, typically methanol, ethanol or 1- or 2-propanol, nitrites, typically acetonitrile, halogenated hydrocarbons, typically dichloromethane, acid amides, typically dimethylformamide, bases, typically heterocyclic nitrogen bases, e.g. pyridine, carboxylic acids, typically lower alkanecarboxylic acids, e.g. acetic acid, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process. Such solvent mixtures may also be used in processing, for example through chromatography or distribution.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described hereinabove as preferred, particularly as especially preferred, primarily preferred, and/or preferred above all.

In the preferred embodiment, a compound of formula I is prepared according to or in analogy to the processes and process steps defined in the Examples.

The compounds of formula I, including their salts, are also obtainable in the form of hydrates, or their crystals can include for example the solvent used for crystallization (present as solvates).

Pharmaceutical Preparations, Methods, and Uses

The present invention relates also to pharmaceutical compositions that comprise a compound of formula I as active ingredient and that can be used especially in the treatment of the diseases mentioned herein. Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions comprise the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to pharmaceutical compositions for use in a method for the prophylactic or especially therapeutic management of the human or animal body, to a process for the preparation thereof (especially in the form of compositions for the treatment of tumors) and to a method of treating tumor diseases, especially those mentioned hereinabove.

Pharmaceutical preparations contain from about 0.000001% to 95% of the active ingredient, whereby single-dose forms of administration preferably have from approximately 0.00001% to 90% and multiple-dose forms of administration preferably have from approximately 0.0001 to 0.5% in the case of preparations for parenteral administration or 1% to 20% active ingredient in the case of preparations for enteral administration. Unit dose forms are, for example, coated and uncoated tablets, ampoules, vials, suppositories or capsules. Further dosage forms are, for example, ointments, creams, pastes, foams, tinctures, lipsticks, drops, sprays, dispersions, etc. Dose unit forms, such as coated tablets, tablets or capsules, contain about 0.0025 g to about 0.1 g of the active ingredient.

The pharmaceutical preparations of the present invention are prepared in a manner known per se, for example by means of conventional mixing, granulating, coating, dissolving or lyophilising processes.

Preference is given to the use of solutions of the active ingredient, and also suspensions or dispersions, especially isotonic aqueous solutions, dispersions or suspensions which, for example in the case of lyophilised preparations which contain the active ingredient on its own or together with a carrier can be made up before use. The pharmaceutical preparations may be sterilised and/or may contain excipients, for example preservatives, stabilisers, wetting agents and/or emulsifiers, solubilisers, salts for regulating the osmotic pressure and/or buffers and are prepared in a manner known per se, for example by means of conventional dissolving or lyophilising processes. The said solutions or suspensions may contain viscosity-increasing agents or also solubilisers.

Suspensions in oil contain as the oil component the vegetable, synthetic, or semi-synthetic oils customary for injection purposes. In respect of such, special mention may be made of liquid fatty acid esters that contain as the acid component a long-chained fatty acid having from 8 to 22, carbon atoms. The alcohol component of these fatty acid esters has a maximum of 6 carbon atoms and is a mono- or polyhydric, for example a mono-, di- or trihydric, alcohol, especially glycol and glycerol.

Pharmaceutical compositions for oral administration can be obtained, for example, by combining the active ingredient with one or more solid carriers, if need be granulating a resulting mixture, and processing the mixture or granules, if desired, to form tablets or tablet cores, if need be by the inclusion of additional excipients.

Orally administrable pharmaceutical compositions also include hard capsules consisting of gelatin, and also soft, sealed capsules consisting of gelatin and a plasticiser, such as glycerol or sorbitol. In soft capsules, the active ingredient is preferably dissolved or suspended in suitable liquid excipients, to which stabilisers and detergents may also be added.

Suitable rectally administrable pharmaceutical preparations are, for example, suppositories that consist of a combination of the active ingredient and a suppository base.

The formulations suitable for parenteral administration are primarily aqueous solutions ([or example in physiological saline, obtainable by diluting solutions in polyethylene glycol, of an active ingredient in water-soluble form, e.g. a water-soluble salt, or aqueous injectable suspensions containing-viscosity-increasing agents and where appropriate stabilisers. The active ingredient, if need be together with excipients, can also be in the form of a lyophilisate. Solutions such as those used, for example, for parenteral administration can also be employed as infusion solutions.

The invention relates likewise to a process or a method for the treatment of one of the pathological conditions mentioned hereinabove, especially a corresponding neoplastic disease. The compounds of formula I or can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.001 g to approximately 0.5 g, preferably from approximately 0.005 g to approximately 0.25 g, of a compound of the present invention.

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the formula II and III are known, commercially available, or can be synthesized in analogy to or according to methods that are known in the art.

The aldehyde of formula II, wherein $R_1$ is hydrogen or lower alkyl which is unsubstituted or substituted by hydroxy, lower acyloxy, lower alkoxy, halogen, amino, lower alkyl amino, di-lower alkyl amino, lower acyl amino, $R_2$ is unsubstituted or substituted heteroaryl, Z is O or a bond, can be obtained, e.g., by a process, wherein an epothilone of formula V

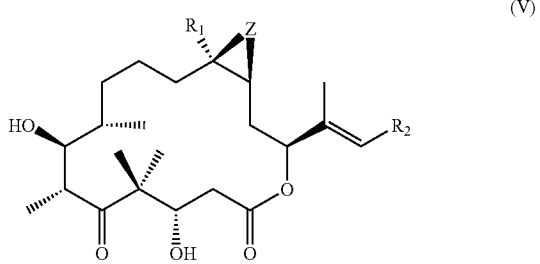

(V)

wherein the radicals $R_1$, $R_2$ and Z have the meanings as provided for a compound of formula II above, is first reacted with a reagent effecting a retro-aldol reaction furnishing an ester of formula VI

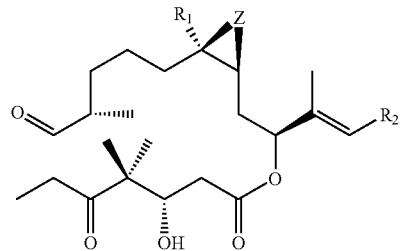

(VI)

wherein the radicals $R_1$, $R_2$ and Z have the meanings as provided for a compound of formula II above, which ester is hydrolized in a second step into its components, 4,4-dimethyl-3-hydroxy-5-oxo-heptanoic acid and the aldehyde of formula II as defined above.

Epothilones of formula V which are suitable as starting material for the preparation of an aldehyde of formula II (see above) are disclosed in J. Org. Chem. 2002, 67, 7730-7736, WO 93/10121, WO97/19086, WO98/38192, WO 98/08849, WO 98/25929, WO 98/22461, WO99/65013, WO 99/02514, WO 99/01124, WO 99/43653, WO99/07692, WO99/67252, WO99/67253, WO00/37473, WO 00/31247 and U.S. Pat. No. 6,194,181 in each case in particular in the compound claims and the final products of the working examples. The subject-matter of the final products of the examples and the claims is hereby incorporated into the present application by reference to this publications. Comprised are likewise the corresponding stereoisomers as well as the corresponding crystal modifications, e.g. solvates and polymorphs, which are disclosed therein.

An ethylketone of formula III,

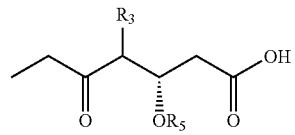

(III)

wherein $R_5$ is a protecting group and $R_3$ has the meaning as provided above for a compound of formula I, can be prepared, e.g., as described in WO99/07692 on pages 20 to 26 or JP3048641.

An ethylketone of formula III, wherein $R_3$ is methyl, $R_5$ is TBDMS and the stereocenter in 4-position having the (S)-configuration, can be prepared, starting with the carboxylic acid ester of formula VII

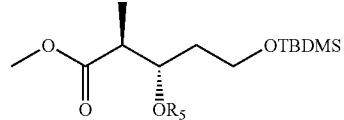

(VII)

wherein $R_5$ represents TBDMS (preparation described by S. Ali and G. Georg in Tetrahedron Letters 38, 10, 1997, 1703-1706, Scheme 2).

In a first step, the carboxylic acid ester of formula VII, wherein $R_5$ represents TBDMS, is transferred into the amide of formula VIII,

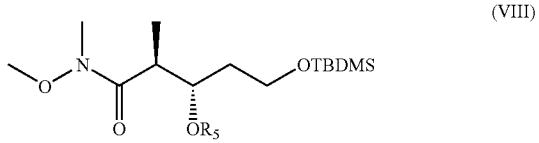

wherein $R_5$ represents TBDMS, by reaction in a suitable solvent like toluene or benzene with N,O-dimethylhydroxylamine hydrochloride in the presence of an equal amount of trimethylaluminium at a temperature between −10° C. and +10° C., e.g. about 0° C.

The obtained amide of formula VII, wherein $R_5$ represents TBDMS, is then in a second step subject of a Grignard reaction employing ethylmagnesium bromide or ethyllithium under conditions known as such, e.g. a solution of the Grignard reagent in diethylether or tetrahydrofuran is dropped to the solution of the amide of formula VII in the same solvent at a temperature of about 0° C. in which process the reaction mixture can be punctually warmed or iodine can be added in order to start the reaction. The Grignard reaction is stopped after a period of about 0.5 to 3 hours, e.g. after about 1 hour, providing a ketone of formula IX,

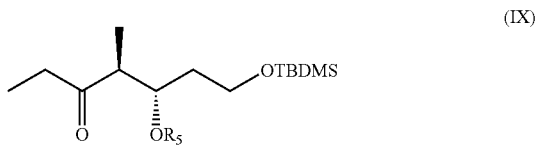

wherein $R_5$ represents TBDMS.

The obtained ketone of formula IX is then oxidised with the Jones reagent in a suitable solvent, e.g. acetone, at a temperature between about −5° C. and +5° C., e.g., 0° C., according to a known procedure (see J. Mulzer et al, J. Org. Chem. 1996, 61, 566-572) furnishing the desired ethylketone of formula III, wherein $R_3$ is methyl, $R_5$ is TBDMS and the stereocenter in 4-position is having the (S)-configuration.

Another synthetic route to the intermediate of formula VII starts in a first step with an antialdol type reaction with an Oppolzer-N-propionyl-sultam to give a sultam of formula X

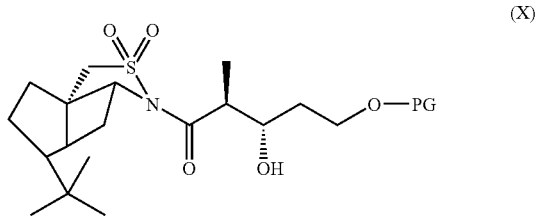

(preparation described by Oppolzer et al, THF 34, 4321 (1993)), which can be transformed via Weinreb amidation and subsequent ethyllithium or ethylmagnesium bromide addition to an intermediate of formula VII.

Furthermore, the present invention pertains to a method of separating C4-desmethyl-epothilone B from epothilone G2, which is characterised by chromatography on a Chiralpak-AD column with an eluant containing a lower alkane, especially hexane, and a lower alkanol, especially 2-propanol.

Additionally, the present invention pertains to a process for the production of C4-desmethyl-epothilone B, which comprises the steps of a) concentrating epothilones in a culture medium for the biotechnological preparation of epothilones, which medium contains a microorganism suitable for the preparation of epothilones, water and other suitable customary constituents of culture media, whereby a cyclodextrin or a cyclodextrin derivative is added to the medium, or a mixture of two or more of these compounds;

b) separating epothilones from one another, which is characterised by chromatography on a reversed-phase column with an eluant containing a lower alkylcyanide, wherein chromatography is carried out on column material charged with hydrocarbon chains, and an eluant containing a lower alkylnitrile is used; and wherein, if desired, further working up steps and purification steps are possible; and c) finally separating C4-desmethyl-epothilone B from epothilone G2, by chromatography on a Chiralpak-AD column with an eluant containing a lower alkane, especially hexane, and a lower alkanol, especially 2-propanol.

EXAMPLES

The following Examples serve to illustrate the invention without limiting the invention in its scope. Temperatures are measured in degrees Celsius (° C.). Unless otherwise indicated, the reactions take place at room temperature.

Abbreviations
d days
DMSO dimethylsulfoxide
EA ethyl acetate
SC flash chromatography
Me methyl
MS mass spectrometry
rpm rotations per minute
RT room temperature
TBDMS tert-butyl-dimethylsilyl
THF tetrahydrofuran
v volume General Methods: For flash chromatography, Kieselgel 60 (40-63 µm), and for thin layer chromatography, DC 60 $F_{254}$-plates from E. Merck (Darmstadt, Germany) are used. All reagents are purchased from Fluka (Buchs, Switzerland).

Example 1

Preparation of C4-Desmethyl-Epothilone B by Fermentation

The volume of harvest from the 500 litre main culture described in Example 2D of WO99/42602 of 450 litres is separated into the liquid phase (centrifugate+rinsing water=650 litres) and solid phase (cells=ca. 15 kg) using a Westfalia clarifying separator Type SA-20-06 (rpm=6500). The main part of the epothilones are found in the centrifugate, The centrifuged cell pulp contains <15% of the determined epothilone portion and is not further processed. The 650 litre centrifugate is then placed in a 4000 litre stirring vessel, mixed with 10 litres of Amberlite XAD-16

(centrifugate:resin volume=65:1) and stirred. After a period of contact of ca. 2 h, the resin is centrifuged away in a Heine overflow centrifuge (basket content 40 litres; rpm=2800). The resin is discharged from the centrifuge and washed with 10-15 litres of deionised water. Desorption of 591.7 kg of charged resin (styrene/divinyl-benzene copolymer resin XAD-16 charged with epothilones from a culture medium) is effected by stirring the resin in two portions each with 720 litres of toluene in four portions for about 8 hours. Separation of the toluene phase from the resin takes place using a suction filter. The combined toluene phases are washed in two portions with each 250 l of water. After phase separation, the toluene extract is concentrated in a 1000 litres reactor to approximately 20-40 litres and afterwards concentrated to dryness in a rotary evaporator under vacuum. The toluene extract is dissolved in 16.5 litres of methanol and 24.5 litres of cyclohexane. After addition of 0.8 litres of water phase separation occurs immediately. The methanol fraction is evaporated to dryness in a rotary evaporator under vacuum. The methanol extract is afterwards being crystallized in a solvent mixture consisting of 2.05 litres isopropanol and 10.25 litres cyclohexane, yielding 0.4 kg crystallized material. The crystals are dissolved in 3.2 litres acetonitrile/water=⅔ (v/v) and the resulting feed solution is transferred in three separate runs onto a preparative reversed phase column (25 kg RP-18 spherical silica gel, YMC-Gel ODS-A 120; 5-15 μm; Waters Corp., Milford, Mass., USA). Elution is effected with acetonitrile/water=⅔ (v/v) as mobile phase with a flow rate of 2.7 litres/min; retention time of C4-desmethyl-epothilone B and epothilone G2 58-65 min. Fractionation is monitored with a UV detector at 250 nm. The acetonitrile of the combined fractions (of the three runs) having a retention time between 58-65 min is distilled off providing a mixture of C4-desmethyl-epothilone B and epothilone $G_2$. 3 g of such mixture is separated into its components on a preparative column (40 cm×10 cm I.D.) containing 2.0 kg amylose tris-(3,5-dimethylphenylcarbamate coated on silicagel (Chiralpak-AD®) in three runs (1 g each run; mixture being disolved in 20 ml hexane and 20 ml 2-propanol). Elution is effected with a hexane/2-propanol 9/1 (v/v) mobile phase with a flow rate of 400 ml/min at room temperature. UV-detection occurs at 249 nm. C4-desmethyl-epothilone B elutes between 90 and 110 min. The corresponding fractions are combined and evaporated to dryness at 40° C. under vacuum and the obtained evaporation residue is re-chromatographed 2 times under the same conditions yielding at least 71 mg C4-desmethyl-epothilone B with a purity of >97%; $^1$H-NMR (500 MHz, DMSO-$d_6$; δ/ppm) 7.31 (s, 1H, H19), 6.51 (s, 1H, H17), 5.26 (d, 9.5 Hz, 1H, H15), 5.02 (d, 4.8 Hz, 1H, 3-OH), 4.42 (d, 6.6 Hz, 1H, 7-OH), 4.31 (m, 1H, H3), 3.47 (dd, 9.7 Hz, 6.8 Hz, 1H, H7), 3.14 (m, 1H, H4), 2.89 (m, 1H, H6), 2.84 (dd, 9.9 Hz, 3.3 Hz, 1H, H13), 2.63 (s, 3H, 21-Me), 2.25 (dd, 14.9 Hz, 10.5 Hz, 1H, H2), 2.10 (dd, 14.9 Hz, 2.6 Hz, 1H, H2), 2.08 (s, 3H, 16-Me), 2.05 (m, 1H, H14), 1.76 (m, (m, 1H, H14), 1.50 (m, 1H, H11), 1.40 (m, 1H, H10), 1.34 (m, 1H, H11), 1.32 (m, 1H, H9), 1.29 (m, 1H, H8), 1.16 (s, 3H, 12-Me), 1.13 (m, 1H, H10), 1.11 (d, 7.0 Hz, 3H, 6-Me), 1.05 (m, 1H, H9), 0.93 (d, 6.60 Hz, 3H, 8-Me), 0.89 (d, 7.0 Hz, 3H, 4-Me); ESI+MS: [M+H]$^+$: 494 D; [M+Na]$^+$: 516 D.

Example 2

(2S,6R,7S,9S)-6,7-Epoxy-9-hydroxy-2,6,10-trimethyl-11-(2-methyl-4-thiazolyl)-undec-10-en-1-al 300 mg (0.6 mmol) of the compound from stage 2.1 and 0.5 g of hog liver esterase immobilised on Eupergit C (Fluka; 839 U/g) are suspended in 200 mL of 1N phosphate buffer (pH=7) and stirred for 3 d. The product is extracted with ethyl acetate and purified by means of FC (150 g of silica gel, $CH_2Cl_2 \rightarrow CH_2Cl_2$/acetone=4:1) giving the desired aldehyde as a colorless oil: $R_f$ ($CH_2Cl_2$/acetone=85:15): 0.36; M+H=338; $^1$H-NMR (500 MHz, DMSO-$d_6$; δ/ppm): 9.55 (d, 1.5 Hz, 1H, CHO), 7.29 (s, 1H, H19), 6.44 (1s, 1H, H17), 5.1 (d, 5.5 Hz, 1H, 15-OH), 4.10 (m, 1H, H15), 2.81 (m, 1H, H13), 2.63 (s, 3H20-Me), 2.36 (m, 1H, H8), 1.18 (s, 3H, 12-Me), 0.99 (d, 6Hz, 3H, H9).

Stage 2.1: (3S)-4,4-Dimethyl-3-hydroxy-5-oxo-heptanoic acid ((2S,6R,7S,9S)-6,7-epoxy-2,6,10-trimethyl-11-(2-methyl-4-thiazolyl)-undec-10-en-1-al-9-yl) ester 0.5 g (0.99 mmol) of epothilone B are dissolved in 84 mL of $CH_2Cl_2$. After adding 43 μL (0.44 mmol) of piperidine and 127 μL (0.44 mmol) of titanium tetra-isopropylate, the reaction solution is stirred for 16 h at RT. After concentration In vacuo, the product is purified by FC (150 g of silica gel, $CH_2Cl_2 \rightarrow CH_2Cl_2$/acetone=4:1) giving a colorless oil: $R_f$ ($CH_2Cl_2$/acetone=85:15): 0.57; M+H=508; $^1$H-NMR (500 MHz, DMSO-$d_6$; δ/ppm): 9.56 (d, 1.5 Hz, 1H CHO), 7.37 (s, 1H, H19), 6.45 (s, 1H, H17), 5.31 (m, 1H, H15), 5.10 (d, 5.5 Hz, 1H, 3-OH), 4.13 (m, 1H, H3), 2.74 (m, 1H, H13), 2.64 (s, 3H, 20-Me), 2.53 (t, 7.5 Hz, 2H, H6), 2.36 (m, 1H, H8), 2.4/2.21 (m/m, 2H, H2), 2.06 (s, 3H, 16-Me), 1.98/1.77 (m/m, 2H, H14), 1.67/1.34 (m/m, 2H, H9), 1.45 (m, 2H, H10), 1.18 (s, 3H, 4-Me), 1 (s/s/s, 9H, 4-Me, 8-Me, 12-Me), 0.87 (t, 7.5 Hz, 3H, 6-Me).

Example 3

(2S,6R,7S,9S)-6,7-Epoxy-9-hydroxy-2,10-dimethyl-11-(2-methyl-4-thiazolyl)-undec-10-en-1-al 550 mg (1.12 mmol) of the compound from stage 3.1 is dissolved in a mixture of 200 mL of acetonitrile and 2 mL of 2N NaOH and stirred for 3 d. The product is extracted with ethyl acetate and purified by FC (150 g of silica gel, $CH_2Cl_2 \rightarrow CH_2Cl_2$/acetone=4:1) giving the desired aldehyde a colorless oil: $R_f$ ($CH_2Cl_2$/acetone=85:15): 0.27; M+H=324; $^1$H-NMR (500 MHz, DMSO-$d_6$; δ/ppm): 9.56 (d, 1.5 Hz, 1H, CHO), 7.29 (1s, 1H, H19), 6.45 (s, 1H, H17), 5.11 (d, 5.5Hz, 15-OH), 4.13 (m, 1H, H15), 3.0 (m, 1H, H13), 2.87 (s, 1H, H12), 2.63 (s, 3H, 20-Me), 2.36 (m, 1H, H8), 1.69 (m, 2H, H14), 0.99 (d, 6 Hz, 3H, H9).

Stage 3.1: (3S)-4,4-Dimethyl-3-hydroxy-5-oxo-heptanoic acid ((2S,6R,7S,9S)-6,7-epoxy-2,10-dimethyl-11-(2-methyl4-thiazolyl)-undec-10-en-1-al-9-yl) ester 1 g (2.03 mmol) of epothilone A is dissolved in 168 mL of $CH_2Cl_2$. After adding 86 μl (0.88 mmol) of piperidine and 254 μl (0.88 mmol) of titanium tetra-isopropylate, the reaction solution is stirred for 16 h at RT. After concentration in vacuo, the product is purified by FC (200 g of silica gel, $CH_2Cl_2 \rightarrow CH_2Cl_2$/acetone=4:1) giving a colorless oil: $R_f$ ($CH_2Cl_2$/acetone=85:15): 0.55; M+H=494.

Example 4

The following aldehydes of formula II, wherein $R_4$ is H, can be prepared using the procedure described in Examples 2 and 3 and using instead of epothilone A or B as the starting material a compound of formula V listed in Table 1.

TABLE 1

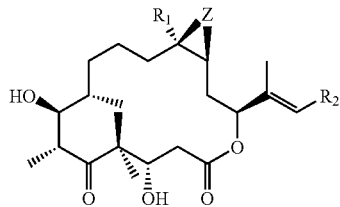

(V)

|  |  |  |  | Aldehyde of formula II, $R_4$ = H | | |
|---|---|---|---|---|---|---|
| Ex. | $R_1$ | $R_2$ | Z | $R_1$ | $R_2$ | Z |
| 4.1 | Me | 2-ethyl-4-thiazolyl | O | Me | 2-ethyl-4-thiazolyl | O |
| 4.2 | Me | 2-methylthio-4-thiazolyl | O | Me | 2-methylthio-4-thiazolyl | O |
| 4.3 | Me | 2-methyl-4-oxazolyl | O | Me | 2-methyl-4-oxazolyl | O |
| 4.4 | Me | 2-methyl-benzothiazol-5-yl | O | Me | 2-methyl-benzothiazol-5-yl | O |
| 4.5 | Me | 2-methyl-benzothiazol-6-yl | O | Me | 2-methyl-benzothiazol-6-yl | O |
| 4.6 | Me | 5-methyl-2-pyridinyl | O | Me | 5-methyl-2-pyridinyl | O |
| 4.7 | Me | 2-aminomethyl-4-thiazolyl | O | Me | 2-aminomethyl-4-thiazolyl | O |
| 4.8 | Me | 2-dimethylamino-4-thiazolyl | O | Me | 2-dimethylamino-4-thiazolyl | O |
| 4.9 | Me | 2-fluoromethyl-4-thiazolyl | O | Me | 2-fluoromethyl-4-thiazolyl | O |
| 4.10 | Me | 2-methyl-4-thiazolyl | bond | Me | 2-methyl-4-thiazolyl | bond |
| 4.11 | H | 2-ethyl-4-thiazolyl | O | H | 2-ethyl-4-thiazolyl | O |
| 4.12 | H | 2-methylthio-4-thiazolyl | O | H | 2-methylthio-4-thiazolyl | O |
| 4.13 | H | 2-methyl-4-oxazolyl | O | H | 2-methyl-4-oxazolyl | O |
| 4.14 | H | 2-methyl-benzothlazol-5-yl | O | H | 2-methyl-benzothiazol-5-yl | O |
| 4.15 | Me | 2-methyl-benzothiazol-6-yl | O | Me | 2-methyl-benzothiazol-6-yl | O |
| 4.16 | H | 5-methyl-2-pyridinyl | O | H | 5-methyl-2-pyridinyl | O |
| 4.17 | H | 2-aminomethyl-4-thiazolyl | O | H | 2-aminomethyl-4-thiazolyl | O |
| 4.18 | H | 2-dimethylamino-4-thiazolyl | O | H | 2-dimethylamino-4-thiazolyl | O |
| 4.19 | H | 2-fluoromethyl-4-thiazolyl | O | H | 2-fluoromethyl-4-thiazolyl | O |
| 4.20 | H | 2-methyl-4-thiazolyl | bond | H | 2-methyl-4-thiazolyl | O |
| 4.21 | Me | 2-methyl-benzothiazol-5-yl | bond | Me | 2-methyl-benzothiazol-5-yl | bond |

Example 5

TBDMS-Ether

Aldehydes of formula II wherein $R_4$ is TBS can be obtained in accordance with the procedure described in Example 1c of WO 00/37473 using the aldehydes of formula II from Example 4 as starting materials.

| | Aldehyde of formula II, $R_4$ = H, from Examples 4.1 to 4.21, 2 and 3 | | | Aldehyde of formula II, $R_4$ = TBS | | |
|---|---|---|---|---|---|---|
| Ex. | $R_1$ | $R_2$ | Z | $R_1$ | $R_2$ | Z |
| 5.1 | Me | 2-ethyl-4-thiazolyl | O | Me | 2-ethyl-4-thiazolyl | O |
| 5.2 | Me | 2-methylthio-4-thiazolyl | O | Me | 2-methylthio-4-thiazolyl | O |
| 5.3 | Me | 2-methyl-4-oxazolyl | O | Me | 2-methyl-4-oxazolyl | O |
| 5.4 | Me | 2-methyl-benzothiazol-5-yl | O | Me | 2-methyl-benzothiazol-5-yl | O |
| 5.5 | Me | 2-methyl-benzothiazol-6-yl | O | Me | 2-methyl-benzothiazol-6-yl | O |
| 5.6 | Me | 5-methyl-2-pyridinyl | O | Me | 5-methyl-2-pyridinyl | O |
| 5.7 | Me | 2-aminomethyl-4-thiazolyl | O | Me | 2-aminomethyl-4-thiazolyl | O |

-continued

| | Aldehyde of formula II, $R_4$ = H, from Examples 4.1 to 4.21, 2 and 3 | | | Aldehyde of formula II, $R_4$ = TBS | | |
|---|---|---|---|---|---|---|
| Ex. | $R_1$ | $R_2$ | Z | $R_1$ | $R_2$ | Z |
| 5.8 | Me | 2-dimethylamino-4-thiazolyl | O | Me | 2-dimethylamino-4-thiazolyl | O |
| 5.9 | Me | 2-fluoromethyl-4-thiazolyl | O | Me | 2-fluoromethyl-4-thiazolyl | O |
| 5.10 | Me | 2-methyl-4-thiazolyl | bond | Me | 2-methyl-4-thiazolyl | bond |
| 5.11 | H | 2-ethyl-4-thiazolyl | O | H | 2-ethyl-4-thiazolyl | O |
| 5.12 | H | 2-methylthio-4-thiazolyl | O | H | 2-methylthio-4-thiazolyl | O |
| 5.13 | H | 2-methyl-4-oxazolyl | O | H | 2-methyl-4-oxazolyl | O |
| 5.14 | H | 2-methyl-benzothiazol-5-yl | O | H | 2-methyl-benzothiazol-5-yl | O |
| 5.15 | Me | 2-methyl-benzothiazol-6-yl | O | Me | 2-methyl-benzothiazol-6-yl | O |
| 5.16 | H | 5-methyl-2-pyridinyl | O | H | 5-methyl-2-pyridinyl | O |
| 5.17 | H | 2-aminomethyl-4-thiazolyl | O | H | 2-aminomethyl-4-thiazolyl | O |
| 5.18 | H | 2-dimethylamino-4-thiazolyl | O | H | 2-dimethylamino-4-thiazolyl | O |
| 5.19 | H | 2-fluoromethyl-4-thiazolyl | O | H | 2-fluoromethyl-4-thiazolyl | O |
| 5.20 | H | 2-methyl-4-thiazolyl | bond | H | 2-methyl-4-thiazolyl | bond |
| 5.21 | Me | 2-methyl-benzothiazol-5-yl | bond | Me | 2-methyl-benzothiazol-5-yl | bond |
| 5.22 | Me | 2-methyl-4-thiazolyl (from Example 2) | O | Me | 2-methyl-4-thiazolyl | O |
| 5.23 | H | 2-methyl-4-thiazolyl (from Example 3) | O | H | 2-methyl-4-thiazolyl | O |

Example 6

(3S,4S)-3-Tert-butyl-dimethylsilyloxy-4-methyl-5-oxo-heptanoic acid

The title compound can be obtained by using the procedure described in Example 2.1 with the title compound from Example 1 as the starting material. The free hydroxy group of the product of this first stage can be transferred into the corresponding TBDMS ether by the reaction procedure described in Example 5. After reaction with hog liver esterase immobilised on Eupergit C (Fluka; 839 U/g) in 1N phosphate buffer (pH=7), the work-up procedure is modified in order to obtain the title compound instead of the aldehyde.

Example 7

4,8-Dihydroxy-5,5,7,9,13-pentamethyl-16-(2-methyl-benzothiazol-5-yl)-oxacyclohexadec-13-en-2,6-dione (Reference Example)

0.175 ml of trifluoroacetic acid are added dropwise over the course of 5 minutes at −20° C. to a solution of 0.041 g of the protected lactone of stage 7.3 in 0.7 ml of $CH_2Cl_2$, and the solution is subsequently stirred for 1 h at 0° C. The solution is then concentrated by evaporation, and the residue obtained is purified by FC in $CH_2Cl_2$/methanol 100/1→100/2. The title compound is obtained as a colourless resin; ESI-MS: 502 (M+H)$^+$. $^1$H-NMR (CDCl$_3$, 300 MHz), δ (ppm vs. TMS): 7.99 (s, 1H); 7.80 (d, 1H); 7.36 (d, 1H); 5.92 (d,d, 1H); 5.15-5.28 (m, 1H); 4.21 (d,d, 1H); 3.75 (t, 1H); 3.1-3.23 (m, 1H); 2.84 (s, 3H); 1.70 (s, ~3H). $[α]_D$=−77.39° (c=0.115 in CHCl$_3$).

Stage 7.1: Carboxylic Acid 3.41 ml of a 1.6 M solution of n-butyllithium in THF is added dropwise at 0° C. over 15 minutes to a solution of 0.771 ml of N,N-diisopropyl-ethylamine in 6 ml of THF. The solution is stirred for 10 minutes at −4° C./−5° C. and then cooled to −78° C. At this temperature, a solution of 0.660 g of 4,4-dimethyl-3-(tert-butyl-dimethylsilyloxy)-5-oxo-heptanoic acid is added, the solution is then allowed to warm to −40° C. for 15 minutes, and is subsequently cooled again to −78° C. 3 ml of a solution of 0.608 g of the aldehyde of Ex. 5.21 in THF are subsequently added and the solution is stirred for 30 minutes at −78° C. The reaction is stopped by adding 7 ml of saturated aqueous NH$_4$Cl solution and, after heating to RT, the solution is mixed with 0.513 ml of acetic acid and extracted with EA. The combined organic extracts are dried over Na$_2$SO$_4$, the solvent evaporated, and the remaining oily residue purified by FC in toluene/EA 1/1. The obtained aldol product is dissolved in 40 ml of $CH_2Cl_2$ and the solution mixed with 0.435 ml of 2,6-lutidine. After cooling to 0° C., 0.720 ml of TBS triflate are added and the mixture is stirred for 2½ h at 0° C. After adding 8 ml of 20% citric acid, the organic phase is separated, the aqueous solution back-extracted with $CH_2Cl_2$, dried over Na$_2$SO$_4$ and the solvent evaporated. The remaining oil is taken up in 20 ml of methanol, the solution is mixed with 2.0 g of K$_2$CO$_3$ and 1 ml of water, and the mixture stirred for 90 minutes at RT. Undissolved constituents are filtered off, the pH value of the filtrate is adjusted to 4.5 with Dowex 50W×8 Ion exchanger resin (very acidic cation exchanger with sulphonic acid groups as the active group, matrix of styrene with 8% DVB as crosslinker, Dowex® is a Trademark of Dow Chemical Co.), the resin is filtered off and the new filtrate concentrated by evaporation. The residue is partitioned between 20 ml of $CH_2Cl_2$ and 20 ml of saturated aqueous NH$_4$Cl solution, the organic phase is separated, the aqueous solution back-extracted with $CH_2Cl_2$ and the combined organic extracts are dried over Na$_2$SO$_4$ and concentrated by evaporation. The oil thus obtained is purified by FC in $CH_2Cl_2$/MeOH 99/1→99/2. The opbtained material undergoes the above-described silylation/desilylation sequence a second time. Finally, pure title compound is obtained as an oil; ESI-MS: 862,4 (M+H)+.

Stage 7.2: Hydroxy Acid 1.85 ml of a 1 M solution of tetrabutylammonium fluoride are added to a solution of 0.265 g of the carboxylic acid of stage 7.1 in 6 ml of THF, and stirred for 6 hours at RT. Subsequently, 8 ml of EA and 7 ml of 20% citric acid are added, the organic phase is separated and the aqueous solution back-extracted with EA. The oily residue obtained after drying the combined organic extracts over $Na_2SO_4$ and evaporating the solvent is purified by FC in $CH_2Cl_2$/methanol 98/2→97/3. 17 is obtained as an oil. ESI-MS: 748.3 (M+H)+. $^1$H-NMR ($CDCl_3$, 200 MHz), δ (ppm vs. TMS): 8.23 (d, 1H); 7.76 (d, 1H); 7.40 (d,d, 1H); 5.24 (t, 1H); 4.73-4.84 (m, 1H); 4.45 (t, 1H); 3.67-3.74 (m, 1H); 3.10-3.22 (m, 1H); 2.82 (s, 3H); 1.75 (s, 3H); 1.14 (d, 3H); 1.08 (d, 3H); 0.80-0.95 (m, ca. 24H); 0.10 (s, 3H); 0.05 (s, 3H); 0.04 (s, 3H); 0.01 (s, 3H).

Stage 7.3: 4,8-Bis-(tert-butyl-dimethylsilyloxy)-5,5,7,9,13-pentamethyl-16-(2-methyl-benzothiazol-5-yl)-oxacyclohexadec-13-en-2,6-dione 0.0866 ml of triethylamine and 0.0677 ml of 2,4,6-trichlorobenzoyl chloride (Aldrich, Buchs, Switzerland) are added to a solution of 0.216 g of the carboxylic acid of stage 7.1 in 3 ml of THF, which has been cooled to 0° C., and the solution is stirred for 1 h at 0° C. The solution is subsequently added dropwise at RT over 5 minutes to a solution of 0.354 g of N,N-dimethylaminopyridine in toluene and stirred for 15 h at RT. The solid residue obtained after concentrating the suspension by evaporation at 35° C. is suspended in 30 ml of hexane/ether 3/2, filtered and the residue of filtration is washed twice, each time with 15 ml of the same solvent mixture. The combined filtrate is evaporated to dryness and the solid residue is purified by FC twice in toluene/acetone 100/1.25→100/5 or 100/1→100/4, providing the title compound as a colourless resin; ESI-MS: 730 (M+H)+. $^1$H-NMR ($CDCl_3$, 200 MHz), δ (ppm vs. TMS): 7.97 (s, 1H); 7.79 (d, 1H); 7.37 (d, 1H); 5.59 (d, 1H); 5.25 (t, 1H); 3.93-4.0 (m, 1H); 3.90 (d, 1H); 2.85 (s, 3H); 1.71 (s, 3H). $[α]_D$=−60.72 ° (c=0.415 in $CHCl_3$).

Example 8-30

C4-Desmethyl-Epothilones

C4-Desmethyl-epothilones of formula I can be prepared according to the procedure described in Example 7 using the aldehydes from Example 5 and the heptanoic acid from Example 6

| | Aldehyde from | C4-Desmethyl-epothilone of formula I, wherein A is O, $R_3$ is lower alkyl and $R_5$ and $R_6$ are hydrogen | | | |
|---|---|---|---|---|---|
| Example | Example | $R_1$ | $R_2$ | | Z |
| 8 | 5.1 | Me | 2-ethyl-4-thiazolyl | | O |
| 9 | 5.2 | Me | 2-methylthio-4-thiazolyl | | O |
| 10 | 5.3 | Me | 2-methyl-4-oxazolyl | | O |
| 11 | 5.4 | Me | 2-methyl-benzothiazol-5-yl | | O |
| 12 | 5.5 | Me | 2-methyl-benzothiazol-6-yl | | O |
| 13 | 5.6 | Me | 5-methyl-2-pyridinyl | | O |
| 14 | 5.7 | Me | 2-aminomethyl-4-thiazolyl | | O |
| 15 | 5.8 | Me | 2-dimethylamino-4-thiazolyl | | O |
| 16 | 5.9 | Me | 2-fluoromethyl-4-thiazolyl | | O |
| 17 | 5.10 | Me | 2-methyl-4-thiazolyl | | bond |
| 18 | 5.11 | H | 2-ethyl-4-thiazolyl | | O |
| 19 | 5.12 | H | 2-methylthio-4-thiazolyl | | O |
| 20 | 5.13 | H | 2-methyl-4-oxazolyl | | O |
| 21 | 5.14 | H | 2-methyl-benzothiazol-5-yl | | O |
| 22 | 5.15 | Me | 2-methyl-benzothiazol-6-yl | | O |
| 23 | 5.16 | H | 5-methyl-2-pyridinyl | | O |
| 24 | 5.17 | H | 2-aminomethyl-4-thiazolyl | | O |
| 25 | 5.18 | H | 2-dimethylamino-4-thiazolyl | | O |
| 26 | 5.19 | H | 2-fluoromethyl-4-thiazolyl | | O |
| 27 | 5.20 | H | 2-methyl-4-thiazolyl | | bond |
| 28 | 5.21 | Me | 2-methyl-benzothiazol-5-yl | | bond |
| 29 | 5.22 | Me | 2-methyl-4-thiazolyl | | O |
| 30 | 5.23 | H | 2-methyl-4-thiazolyl | | O |

Example 31

(Aldolisation Step: Preparation of C4-BisNor-EPO-B)

A solution of in situ TMS-disilylated 3-(R)-hydroxy-5-oxo-heptanoic acid (2 mmol) in 4 ml of THF, obtained from yeast reduction (Mitsubishi Kasei Corp. JP3048641, 1991-03-03), is cooled to −10° C. and treated with 2.2 mmol of LDA in THF. The solution is stirred for 20 min. and then cooled down to −40° C. To this lithium enolate is added a solution of protected aldehyde of example 5.22 (2.5 mmol) in dry THF.

The reaction mixture is warmed up to −30° C. and kept at this temperature for 2-3 hours. Finally the reaction mixture is quenched with aqueous citric acid solution. The organic phase separated and the aqueous phase is twice extracted with EtOAc. The combined organic phases are carefully concentrated in vacuo. The residue is dissolved in EtOAc and washed with water and brine. The EtOAc phase is dried over anhydrous $Na_2SO_4$ and finally evaporated to dryness to give a viscous oil of the aldol product.

This product is further transformed by selective deprotection at $OR_4$ and macrolactoni-sation he desired bis-nor-Epothilone derivative under similar conditions as described in Example 7

Example 32

C4-BisNor-Epothilones

C4-BisNor-epothilones of formula I can be prepared according to the procedure described in Example 31 using the protected aldehydes from Example 5 and the heptanoic acid from Example 31

| | Aldehyde from | C4-BisNor-epothilone of formula I, wherein A is O and $R_3$, $R_5$ and $R_6$ are hydrogen | | |
|---|---|---|---|---|
| Example | Example | $R_1$ | $R_2$ | Z |
| 32 | 5.1 | Me | 2-ethyl-4-thiazolyl | O |
| 33 | 5.2 | Me | 2-methylthio-4-thiazolyl | O |
| 34 | 5.3 | Me | 2-methyl-4-oxazolyl | O |
| 35 | 5.4 | Me | 2-methyl-benzothiazol-5-yl | O |
| 36 | 5.5 | Me | 2-methyl-benzothiazol-6-yl | O |
| 37 | 5.6 | Me | 5-methyl-2-pyridinyl | O |
| 38 | 5.7 | Me | 2-aminomethyl-4-thiazolyl | O |
| 39 | 5.8 | Me | 2-dimethylamino-4-thiazolyl | O |
| 40 | 5.9 | Me | 2-fluoromethyl-4-thiazolyl | O |

-continued

| | | C4-BisNor-epothilone of formula I, wherein A is O and $R_3$, $R_5$ and $R_6$ are hydrogen | | |
|---|---|---|---|---|
| Example | Aldehyde from Example | $R_1$ | $R_2$ | Z |
| 41 | 5.10 | Me | 2-methyl-4-thiazolyl | bond |
| 42 | 5.11 | H | 2-ethyl-4-thiazolyl | O |
| 43 | 5.12 | H | 2-methylthio-4-thiazolyl | O |
| 44 | 5.13 | H | 2-methyl-4-oxazolyl | O |
| 45 | 5.14 | H | 2-methy-benzothiazol-5-yl | O |
| 46 | 5.15 | Me | 2-methyl-benzothiazol-6-yl | O |
| 47 | 5.16 | H | 5-methyl-2-pyridinyl | O |
| 48 | 5.17 | H | 2-aminomethyl-4-thiazolyl | O |
| 49 | 5.18 | H | 2-dimethylamino-4-thiazolyl | O |
| 50 | 5.19 | H | 2-fluoromethyl-4-thiazolyl | O |
| 51 | 5.20 | H | 2-methyl-4-thiazolyl | bond |
| 52 | 5.21 | Me | 2-methyl-benzothiazol-5-yl | bond |
| 53 | 5.22 | Me | 2-methyl-4-thiazolyl | O |
| 54 | 5.23 | H | 2-methyl-4-thiazolyl | O |

Example 55

Dry Capsules 3000 capsules, each of which contain 0.005 g of one of the C4-desmethyl-epothilone of the formula I mentioned in the preceding Examples as active ingredient, are prepared as follows:

| Composition | |
|---|---|
| Active ingredient | 1.50 g |
| Lactose | 750.00 g |
| Avicel PH 102 (microcrystalline cellulose) | 300.00 g |
| Polyplasdone XL (polyvinylpyrrolidone) | 30.00 g |
| Magnesium stearate | 9.00 g |

Preparation process: The active ingredient is passed through a No. 30 hand screen. The active ingredient, lactose, Avicel PH 102 and Polyplasdone XL are blended for 15 minutes in a mixer. The blend is granulated with sufficient water (about 500 mL), dried in an oven at 35° C. overnight, and passed through a No. 20 screen. Magnesium stearate is passed through a No. 20 screen, added to the granulation mixture, and the mixture is blended for 5 minutes in a mixer. The blend is encapsulated in No. 0 hard gelatin capsules each containing an amount of the blend equivalent to 25 mg of the active ingredient.

Example 56

PEG Solution 5 mg of a C4-desmethyl-epothilone of formula I is dissolved in 98-100% propylene glycol (1.0 ml). The solution is sterile filtered through a 0.22 microns pore size filter and charged to 1 ml ampoules. The filled ampoules are used for storage and shipment. Prior to intravenous administration, the contents of an ampoule are added to 250 to 1000 ml of a 5% glucose solution in water-for-injection.

Example 57

The efficacy of a C4-desmethyl-epothilone of formula I as inhibitor of microtubule depolymerisation can be determined by the test procedure described above. Final assay concentrations of test compound and porcine microtubule protein (Batch #9) were 4 uM and 0.8 mg/ml, respectively.

TABLE 2

| Compound tested | Tubulin Polymerisation (% of control) |
|---|---|
| Example 1 | 93.3 |
| Epothilone A (Reference Example) | 76.5 |
| Epothilone B (Reference Example) | 93.3 |
| Paclitaxel (Reference Example) | 62.1 |

Example 58

The efficacy against tumour cells can be demonstrated in the procedure described above.

TABLE 3

| Cell Growth Inhibition | Example 1 | Epothilone B (Reference Example) | Paclitaxel (Reference Example) |
|---|---|---|---|
| KB-31, $IC_{50}$ (nM) | 0.49 ± 0.05 | 0.28 ± 0.04 | 3.76 ± 0.52 |
| KB-8511, $IC_{50}$ (nM) | 0.80 ± 0.16 | 0.20 ± 0.04 | 739 ± 86 |

What is claimed is:

1. A process for the preparation of an epothilone of formula I,

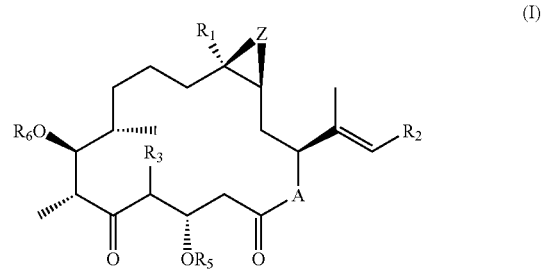

(I)

wherein
A represents O or $NR_7$;
$R_1$ is hydrogen or lower alkyl which is unsubstituted or substituted by hydroxy, lower acyloxy, lower alkoxy, halogen, amino, lower alkyl amino, di-lower alkyl amino or lower acyl amino;
$R_2$ is unsubstituted or substituted heteroaryl having at least one nitrogen atom;
$R_3$ represents hydrogen or lower alkyl;
$R_5$ and $R_6$ are hydrogen; and
$R_7$ is hydrogen or lower alkyl; and
Z is O or a bond; or a pharmaceutically acceptable sale thereof; comprising the steps of:
(a) reacting an aldehyde of formula II

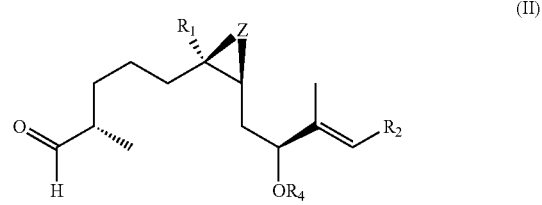

(II)

wherein $R_1$, $R_2$ and Z have the meanings as provided above for a compound of formula I and $R_4$ is a protecting group, with an ethylketone of formula III,

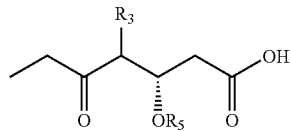

(III)

wherein $R_5$ is H or a protecting group different or identical to $R_4$ and R3 has the meaning as provided above for a compound of formula I, to provide the aldol of formula IV,

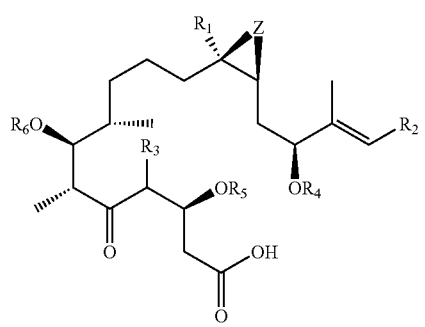

(IV)

wherein $R_1$, $R_2$, $R_3$ and Z have the meanings as provided above for a compound of formula I, $R_4$ a protecting group, $R_5$ is H or a protecting group different or identical to $R_4$ and $R_6$ is hydrogen (b) reacting the aldol of formula IV with a reagent capable to introduce a protecting group which is different or identical to $R_4$ furnishing a carboxylic acid of formula IV, wherein $R_1$, $R_2$, $R_3$ and Z have the meanings as provided above for a compound of formula I, $R_4$ a protecting group and $R_5$ is H or $R_5$ and $R_6$ are protecting groups different or identical to $R_4$;

(c) reacting the carboxylic acid of formula IV with a reagent capable to remove the protecting group $R_4$ under conditions which do not result in the removal of the protecting groups $R_5$ and $R_6$ providing a carboxylic acid of formula IV, wherein $R_1$, $R_2$, $R_3$ and Z have the meanings as provided above for a compound of formula I, $R_4$ is hydrogen and $R_5$ is H or $R_5$ is H or $R_5$ and $R_6$ are protecting groups, (d) macrolactonizing the carboxylic acid of formula IV providing the epothilone of formula I, wherein $R_1$, $R_2$, $R_5$ and Z have the meanings as provided above for a compound of formula I, A is O and $R_5$ is H or $R_5$ and $R_6$ are protecting groups;

(e) reacting the epothilone of formula I with a reagent capable of removing the protecting groups $R_5$ and $R_6$ furnishing an epothilone of formula I, wherein $R_1$, $R_2$, $R_3$, $R_5$, $R_6$ and Z have the meanings as provided above for a compound of formula I and A is O; and (f) optionally reacting the epothilone of formula I into an epothilone of formula I wherein $R_1$, $R_2$, $R_3$, $R_5$, $R_6$ and Z have the meanings as provided above for a compound of formula I and A is $NR_7$, wherein $R_7$ is hydrogen or lower alkyl.

2. An ethylketone of formula III,

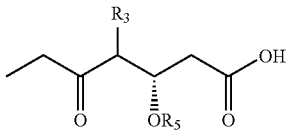

(III)

wherein $R_3$ has the meaning as in claim 1 for a compound of formula I and $R_5$ is hydrogen or a protecting group.

3. An aldol of formula IV,

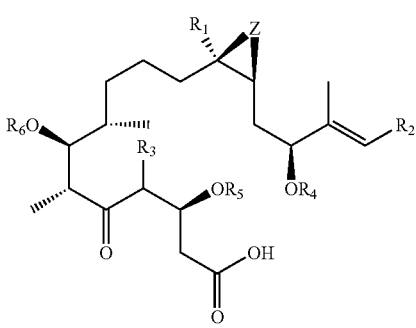

(IV)

$R_1$ is hydrogen or lower alkyl which is unsubstituted or substituted by hydroxy, lower acyloxy, lower alkoxy, halogen, amino, lower alkyl amino, di-lower alkyl amino, lower acyl amino, $R_2$ is unsubstituted or substituted heteroaryl;

$R_3$ represents hydrogen or lower alkyl;

$R_4$ is hydrogen or a protecting group;

$R_5$ is a protecting group different or identical to $R_4$;

$R_6$ is hydrogen or a protecting group different or identical to $R_4$; and

Z is O or a bond.

4. A process for the preparation of an aldehyde of formula II

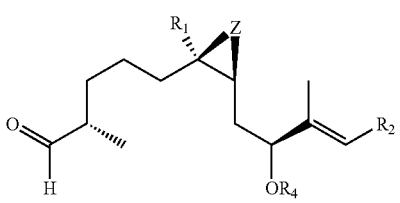

(II)

wherein $R_1$ is hydrogen or lower alkyl which is unsubstituted or substituted by hydroxy, lower acyloxy, lower alkoxy, halogen, amino, lower alkyl amino, di-lower alkyl amino, lower acyl amino;

$R_2$ is unsubstituted or substituted heteroaryl;

Z is O or a bond; comprising the steps of:

(a) reacting an epothilone of formula V

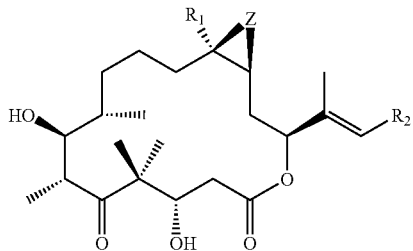
(V)

wherein the radicals $R_1$, $R_2$ and Z have the meanings as provided for a compound of formula II above, with a reagent effecting a retro-aldol reaction furnishing an ester of formula VI

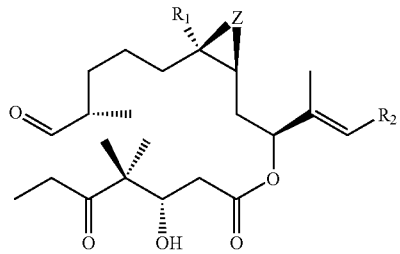
(VI)

wherein the radicals $R_1$, $R_2$ and Z have the meanings as provided for a compound of formula II above, which ester is hydrolized in a second step into its components, 4,4-dimethyl-3-hydroxy-5 oxo-heptanoic acid and the aldehyde of formula II as defined above.

* * * * *